United States Patent
Eccleston et al.

(10) Patent No.: US 7,403,704 B2
(45) Date of Patent: Jul. 22, 2008

(54) DUAL HEATING DEVICE AND METHOD

(75) Inventors: Rolando A. Eccleston, Ann Arbor, MI (US); Richard M. Matovina, Canton, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 532 days.

(21) Appl. No.: 11/184,200

(22) Filed: Jul. 19, 2005

(65) Prior Publication Data

US 2006/0030917 A1 Feb. 9, 2006

Related U.S. Application Data

(60) Provisional application No. 60/599,628, filed on Aug. 6, 2004.

(51) Int. Cl.
*A61F 7/00* (2006.01)
*F24H 13/00* (2006.01)

(52) U.S. Cl. ........................ 392/470; 392/466
(58) Field of Classification Search ................ 392/470, 392/465, 466, 467, 468, 469, 471, 472, 473, 392/474–496

See application file for complete search history.

(56) References Cited

U.S. PATENT DOCUMENTS

| | | | | |
|---|---|---|---|---|
| 3,980,863 A | * | 9/1976 | Wulz et al. | ................... 219/388 |
| 4,138,607 A | | 2/1979 | Engelmann | |
| 4,160,153 A | | 7/1979 | Melander | |
| 4,316,663 A | | 2/1982 | Fischer | |
| 4,414,464 A | * | 11/1983 | Cloutier | ....................... 392/487 |
| 4,755,845 A | | 7/1988 | Taniguchi et al. | |
| 5,161,389 A | | 11/1992 | Rockenfeller et al. | |
| 5,343,012 A | * | 8/1994 | Hardy et al. | ................. 118/725 |
| 5,385,540 A | * | 1/1995 | Abbott et al. | ............... 604/6.13 |

(Continued)

FOREIGN PATENT DOCUMENTS

WO    WO 00/75577    12/2000

(Continued)

OTHER PUBLICATIONS

Terumo Cardiovascular Systems Corporation, *Sarns™ TCM II Cooling and Heating System*, pp. 1-3.

(Continued)

*Primary Examiner*—Daniel L Robinson
(74) *Attorney, Agent, or Firm*—Mark Molton, Esq.; MacMillian, Sobanski & Todd; Gael Diane Tisack, Esq.

(57) ABSTRACT

A dual-channel fluid temperature control apparatus controls temperature of cardiac fluids during surgery using power from an electrical convenience outlet having a power limit. A first pump receives a first heat exchange fluid to selectively pump the first heat exchange fluid within a first circulation channel. A second pump receives a second heat exchange fluid to selectively pump the second heat exchange fluid within a second circulation channel. A first heater unit comprises a first plurality of independently actuatable heating elements each having a respective power consumption. A second heater unit comprises a second plurality of independently actuatable heating elements each having a respective power consumption. A controller selectably actuates the first and second pumps and the first and second pluralities of heating elements to selectably heat or cool the first and second heat exchange fluids such that power draw of all activated pumps and heating elements is maintained within the power limit.

14 Claims, 3 Drawing Sheets

U.S. PATENT DOCUMENTS

| | | | | |
|---|---|---|---|---|
| 5,614,133 | A | * | 3/1997 | Tanaka et al. .................. 264/21 |
| 5,805,856 | A | * | 9/1998 | Hanson ...................... 392/465 |
| 5,891,330 | A | * | 4/1999 | Morris ....................... 210/104 |
| 6,180,000 | B1 | * | 1/2001 | Wilbur et al. ................. 210/85 |
| 6,410,889 | B2 | * | 6/2002 | Davis et al. ................. 219/390 |
| 6,423,268 | B1 | | 7/2002 | King et al. |

OTHER PUBLICATIONS

Terumo Cardiovascular Systems Corporation, *Sarns TCM II Operators Manual*, May 2001, pp. 1-28.

\* cited by examiner

DUAL HEATING DEVICE AND METHOD

CROSS REFERENCE TO RELATED APPLICATIONS

This application claims priority to U.S. provisional application 60/599,628, filed Aug. 6, 2004.

STATEMENT REGARDING FEDERALLY SPONSORED RESEARCH

Not Applicable.

BACKGROUND OF THE INVENTION

The present invention relates in general to cardiac surgery, and, more specifically, to the heating and cooling of blood or other fluids delivered to a patient during cardiac bypass surgery.

Heating and cooling devices are an important part of blood perfusion systems used during cardiac surgery. During surgery, blood is cooled in a bypass circuit to induce hypothermia to protect the organs. A separate cardioplegia circuit typically provides a dedicated flow of cooled solution directly to the heart, at least periodically. When the surgery has been completed, the blood and/or other fluids flowing in the two circuits are heated prior to the patient waking from anesthesia. During various circumstances that may arise during operation of the blood perfusion system, it becomes desirable not only to heat both circuits or cool both circuits simultaneously, but also to cool one circuit while the other is heating or to deactivate one circuit while the other is either heating or cooling.

Conduits carrying the blood and/or cardioplegia in each circuit pass through respective heat exchangers. Water (or other heat exchange fluid) in the two respective heater/cooler circuits is pumped through passages in the heat exchangers for adding heat to or removing heat from the blood/cardioplegia as necessary. An integrated heater/cooler unit having an integrated controller and an integrated power supply usually includes a single ice-bath compartment for selectably cooling the water in both water circuits and a pair of heating devices for selectably heating the water in the two circuits independently.

In view of electrical safety standards and the desire to power a dual heater/cooler unit from a single conventional outlet in an operating room, it is necessary to ensure that the current drawn from the outlet stays safely within a maximum limit. The significant power-consuming elements of the unit are the controller electronics (e.g., microcontroller, display, and other related circuitry), two water-circulating pumps, and two heaters. The cooling function does not consume power other than that to operate the controls and pumps since ice is used as a source of cooling. The maximum current draw occurs when both heaters operate simultaneously (i.e., both the arterial and the cardioplegia patient circuits are being heated and both pumps are operating).

U.S. Pat. No. 6,423,268, issued to King et al., discloses a dual heater wherein circuitry is provided to prevent the first and second heaters from being activated simultaneously. Furthermore, a heater is not activated until after a delay from the time when the other heater is deactivated. Thus, when heating is needed in both fluid circuits, King et al. alternately activates each of the two heaters with a suitable delay time between activations so that instantaneous switching is avoided. By driving the two heaters in a complementary fashion (separated by an off time), both circuits are heated without exceeding the available current. However, a relatively complicated and expensive heater control system including multiple relays is required to obtain the necessary delays. It would be desirable to limit the maximum current draw without such complications or expense.

The relay switching system as implemented in King et al has additional disadvantages. A significant in-rush current may flow when a heater is activated. The in-rush current may lead to the tripping of a circuit breaker and/or excessive generation of heat in the switching device. Due to inherent variations in the timing provided by different relay devices (even of the same manufacturer and part number), significant timing errors may occur when activating the heaters. The errors can become large enough to inadvertently cause the heaters to be activated simultaneously, resulting in an excessive current draw. It would be desirable to eliminate in-rush current and to provide a more precise and robust control of heater currents in order to gain performance benefits and to avoid simultaneous activation errors.

SUMMARY OF THE INVENTION

The present invention has the advantage of limiting current consumption without requiring delays or relay circuits. Innovative new heater structures and power sharing methods are disclosed herein which achieve precise and robust heater control and which eliminate in-rush current.

In one aspect of the invention, a dual-channel fluid temperature control apparatus controls temperature of cardiac fluids during surgery using power from an electrical convenience outlet having a power limit. A first circulation channel conveys a first heat exchange fluid. A second circulation channel conveys a second heat exchange fluid. A first pump receives the first heat exchange fluid to selectively pump the first heat exchange fluid within the first circulation channel. A second pump receives the second heat exchange fluid to selectively pump the second heat exchange fluid within the second circulation channel. A first heater unit is thermally coupled to the first heat exchange fluid and comprises a first plurality of independently actuatable heating elements each having a respective power consumption. A second heater unit is thermally coupled to the second heat exchange fluid and comprises a second plurality of independently actuatable heating elements each having a respective power consumption. A cooling bath is selectably thermally coupled to the first and second heat exchange fluids. A controller selectably actuates the first and second pumps and the first and second pluralities of heating elements to selectably heat or cool the first and second heat exchange fluids such that power draw of all activated pumps and heating elements is maintained within the power limit.

BRIEF DESCRIPTION OF THE DRAWINGS

FIG. 3 is a chart of potential operating modes where heating is required.

DETAILED DESCRIPTION OF PREFERRED EMBODIMENTS

The present invention is a user-selectable water temperature regulation system consisting of two independent channels with equal heating and cooling performance capability. Each channel of the system is capable of operating in two modes referred to as Standby mode and Maintain mode. A Prime mode (wherein the heaters are turned off) may also be provided wherein heat exchange fluid is circulated at a high flow rate through all the flow channels of the system in order to fill the channels with heat exchange fluid and to remove any trapped air.

In Standby mode, the user is able to adjust a setpoint temperature but there is no active regulation of temperature. The pump and heater are turned off for that specific channel. The system electronics including a display and a processor provide a low power draw.

In Maintain mode, the user is able to adjust the setpoint temperature and active regulation of temperature takes place. Depending on whether or not any heating or cooling is needed at any particular time, one or two pumps and one or two heaters may be active. Maximum power draw occurs when both channels are providing maximum heating. The power draw equals the combined consumption of the system electronics, the two pumps, and the two heaters. While it would be possible to size the two heaters so that the power limit of the supply is not exceeded with both channels at maximum heating, it is desirable to have an increased heating capability in each channel so that a greater level of heating can be provided at times that only one channel requires heating.

Figure 1:
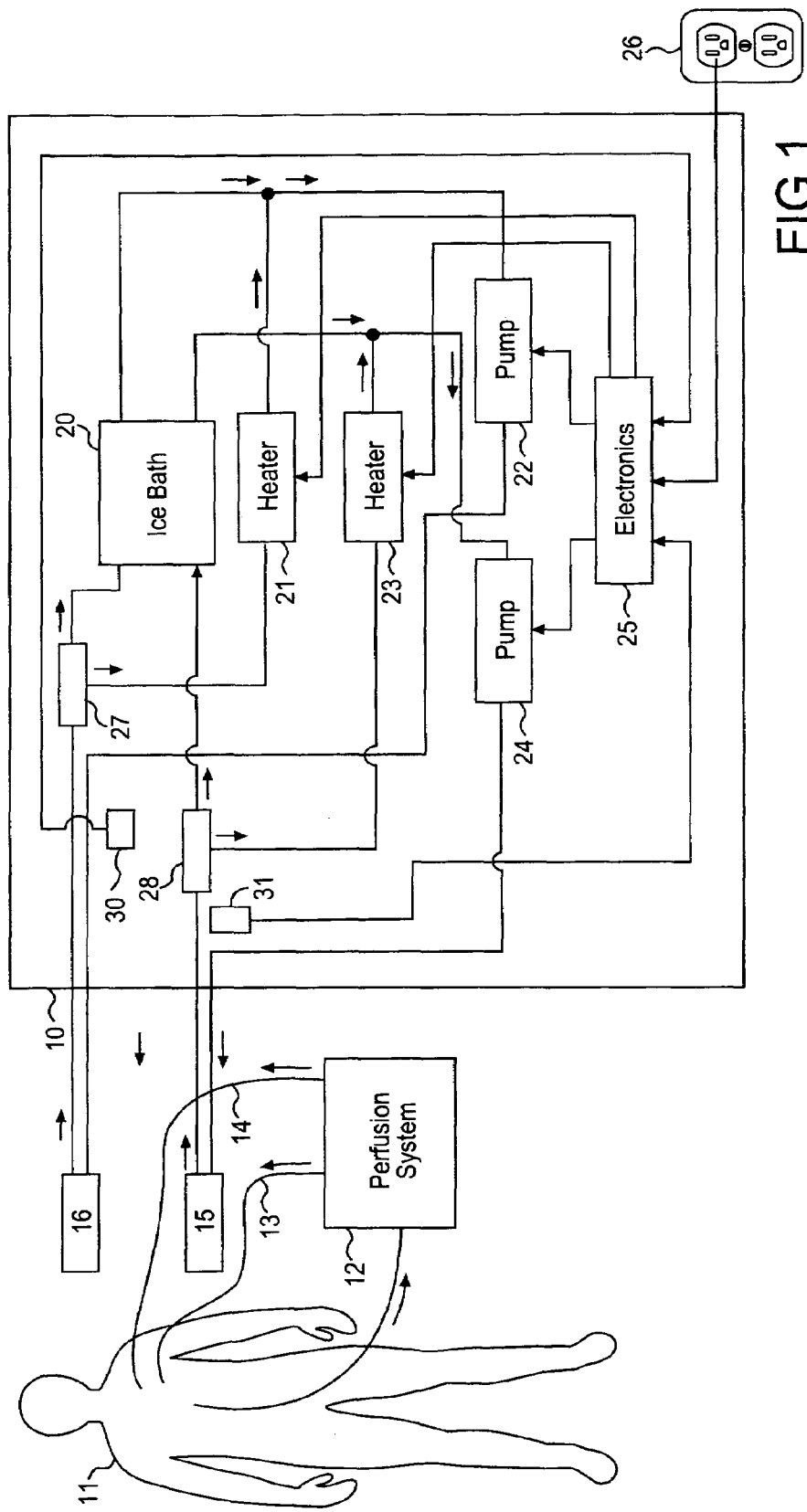
FIG. 1 is a schematic/block diagram of the dual heating/cooling system of the present invention in conjunction with a perfusion system.

Referring to FIG. 1, a dual heater/cooler system 10 may be used in support of cardiac surgery for a patient 11. A perfusion system 12 performs heart and lung functions during surgery by circulating blood from patient 11 through a blood circuit 13 and a cardioplegia circuit 14. Fluids in circuits 13 and 14 may be selectively cooled or heated using heat exchangers 15 and 16, respectively. A heat exchange fluid such as water flows between dual heater/cooler system 10 and heat exchangers 15 and 16 when necessary to achieve a setpoint temperature.

System 10 includes a source of cooling such as an ice bath 20 which can separately cool the heat exchange fluids in each of these separate circulation channels. A first channel connected to heat exchanger 16 includes a first heater 21 and a first pump 22 while a second circulation channel includes second heater 23 and second pump 24. An electronics block 25 is connected to heaters 21 and 23 and to pumps 22 and 24 which receives power from an outlet 26.

In order to properly direct heat exchange fluid flowing in the first circulation channel for either cooling or heating, a valve 27 directs fluid flow through either ice bath 20 or heater 21. Similarly, a valve 28 directs heat exchange fluid in the second circulation channel to ice bath 20 or heater 23. A pair of temperature sensors 30 and 31 are connected to electronics block 25 to provide temperature feedback so that electronics block 25 can control the temperature of the exiting heat exchange fluid to the desired setpoint temperature. Alternatively, remote temperature sensors can be employed.

Figure 2:
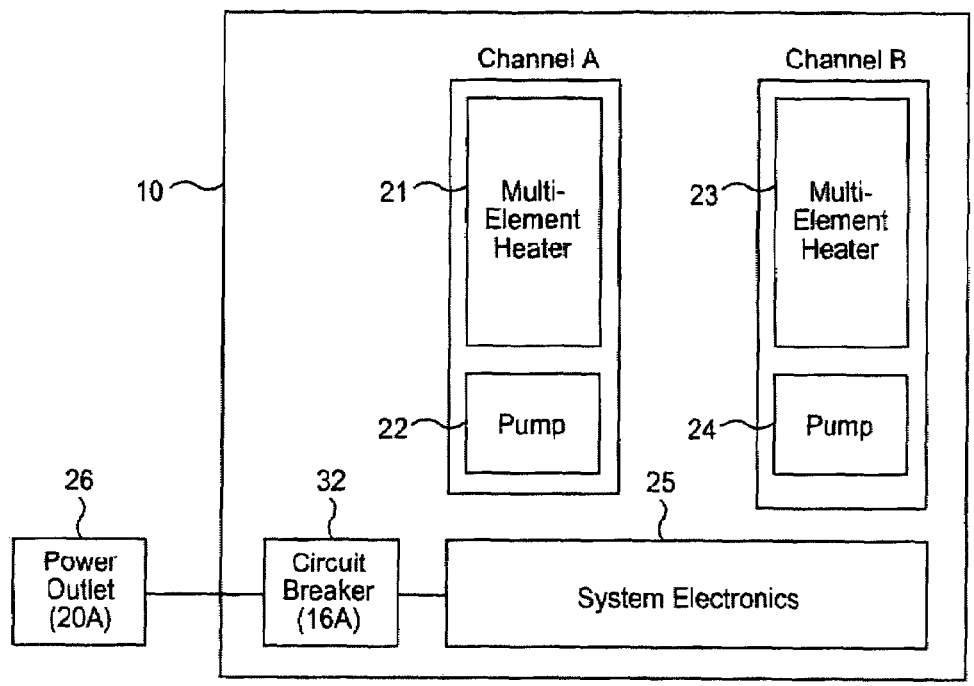
FIG. 2 is a block diagram of the heating/cooling system components.

As shown in FIG. 2, outlet 26 typically provides a current limit of about 20 amps. A circuit breaker 32 is provided in system 10 for limiting current drawn by system 10 to 16 amps, or about 1,750 watts. The three main components of power consumed by system 10 are the system electronics (e.g., display, controller, interface, and status circuitry), pumps and heaters. Since the cooling source is operator-added ice, cooling does not require electrical power beyond that for the electronics and pump. System electronics typically draw about 0.5 amps or about 50 watts and each pump draws about 2 amps or 225 watts. The numerical examples given herein are for illustration only and they are only approximate since a range of input voltages can be utilized.

When heating is not required in either circulation channel, then power consumption is no greater than that drawn by the electronics and both pumps operating simultaneously (if both channels are actively cooling), which requires about 500 watts. That is well within the available 1750 watts. When heating is required, however, it becomes necessary to insure that power consumption is kept within the available power. In the operating modes to be discussed, it is assumed that the two channels are identical and therefore it does not matter which channel is heating or cooling. Only how many channels are requiring heating is important. Thus, the channel labels A and B in FIGS. 2 and 3 are interchangeable.

The operating modes of the present invention for which it is necessary to manage power consumption during heating are shown in FIG. 3. Thus, in mode 1, one channel is in standby (i.e., neither the pump nor the heater are activated) and the other channel is in maintain mode (its pump is operating continuously and heating may be required depending upon the sensed temperature). In mode 2, one channel is in maintain mode with heating required and the other channel is in maintain mode but only cooling is required (i.e., the other channel draws power for operating the pump only). In mode 3, both channels are in maintain mode with heating required (i.e., both pumps and both heaters are activated).

For the purposes of managing power consumption during heating, each heater of the present invention includes a plurality of independently actuatable heating elements with each element having a respective power consumption. The system controller activates selected ones of the heating elements when heating is required so that the activated heating elements have a combined maximum power consumption that maintains power draw within the power limit of the power supply. In a preferred embodiment, the size (i.e., power consumption) of individual heating elements is chosen such that when both channels are simultaneously heating then respective heating elements in each heater may be turned on continuously such that a power draw is maintained substantially equal to the power limit. Alternatively, and during other modes of operation, the heating elements may also be rapidly turned on and off (i.e., modulated) to obtain heating energy less than the maximum for a particular heating element.

Figure 4:
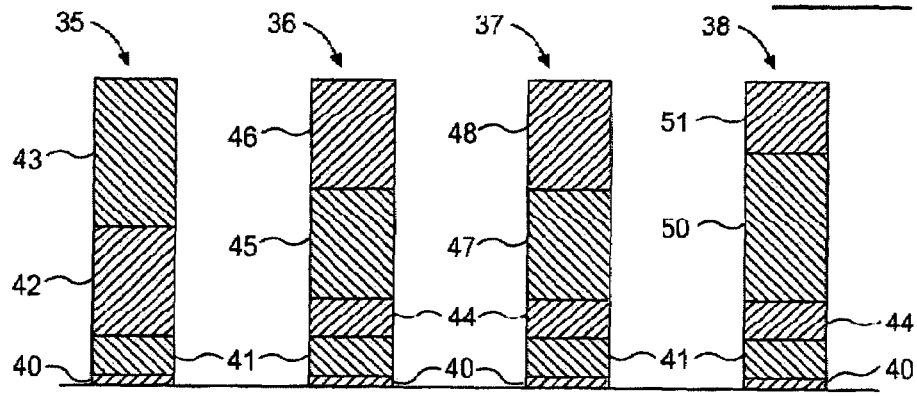
FIG. 4 is a chart of relative power consumption of various system components in each of the operating modes.

FIG. 4 shows a bar chart for illustrating power usage in various modes of operation. The full height of each bar represents the maximum power available (e.g., 1,750 watts). Bar 35 represents mode 1 wherein one channel is on standby and the other channel requires heating in the maintain mode. Power consumption 40 represents the power consumed by system electronics (e.g., about 50 watts) and power consumption 41 represents power utilized by the pump in the channel requiring heating (e.g., 225 watts). Power consumption 42 represents one heating element in the active heater and power consumption 43 represents power consumed by a second heating element in that heater.

In mode 1 represented by bar 35, about 1500 watts remain available for use by the heating elements in the heating channel. In this particular embodiment, a two element heater is provided with the elements sized to use the full amount of available power when both are activated in mode 1. Thus, power consumption 42 preferably corresponds to a power consumption of 625 watts of a first heating element and power consumption 43 corresponds to a power consumption of 875 watts of a second heating element. When less than maximum heating is required, then power to either or both heating element can be modulated (e.g., pulse width modulated).

Bar 36 corresponds to mode 3 wherein both channels are in maintain mode and require heating. Thus, power consumption 40 represents system electronics, power consumption 41 represents one pump and power consumption 44 represents the other pump. About 1,250 watts remain available for use by the dual heaters. Each heater has an element sized to consume one half of this available power so that the two heaters combine to fully use the available power. In bar 36, power consumption 45 represents 625 watts utilized by one heater and power consumption 46 represents 625 watts utilized by the other heater. Each heating element of the respective heaters may be modulated to produce lesser amounts of heat as required, but total power draw is maintained within the power limit even when each heating element is on continuously.

Bar 37 represents operation in mode 2 according to a first embodiment. Since heating is required only in one channel in mode 2, more than one of the 625 watt and 875 watt heating elements can be actuated in the channel requiring heating (i.e., 1250 watts are available). Thus, power consumption 47 represents full activation of the 625 watt heating element and power consumption 48 represents modulation of the 875 watt heating element so that its consumption is reduced to 625 watts at maximum. Bar 38 shows an alternative embodiment wherein the 875 watt heating element is continuously on as represented by power consumption 50 having a size corresponding to 875 watts. The smaller heating element is modulated to provide a power consumption 51 of about 375 watts.

By appropriately sizing heating elements using two heating elements per heater, minimal use of power modulation is needed for maintaining power draw within the available power limit. Further, since power modulation is not required in both heaters simultaneously for maintaining power draw within the limit, both heaters can be on simultaneously and there is no need for switching delays as was used in the prior art.

Figure 5:
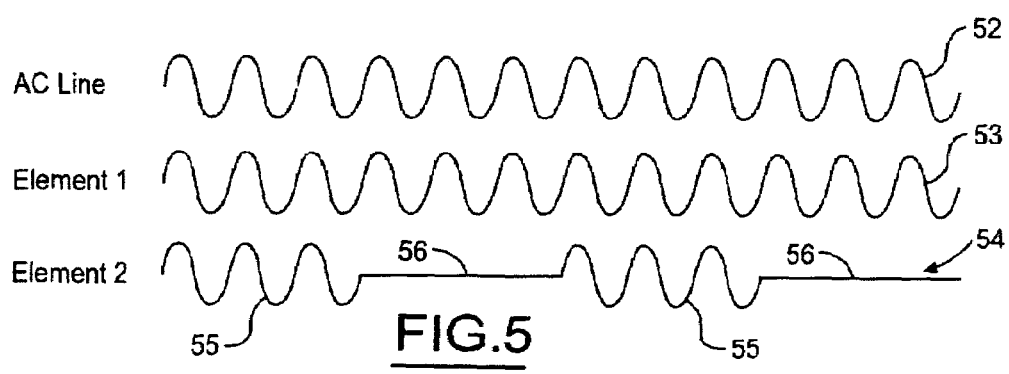
FIG. 5 is a waveform diagram showing input voltage and voltages applied to heating elements in a single heater for limiting power consumption to a power limit.

FIG. 5 shows an AC line voltage 52 that may be directly coupled to a first heating element as shown by waveform 53 for continuous activation at maximum heating. A waveform 54 shows modulation of power delivered to a second element. Using pulse width modulation, the proportion of the power on-time to the sum of the on-time and the off-time corresponds to the percentage of the full power rating that is desired. On-time is shown at wave portions 55 and off-time is shown at wave portions 56. Switching preferably occurs at a zero crossing to eliminate in-rush current stresses in the control electronics.

In other embodiments, other numbers of elements may be included in each heater. For example, a three element embodiment may include in each heater a first heating element of 625 watts, a second heating element of 625 watts, and a third heating element of 250 watts. Such an embodiment can avoid the need for modulating power to maintain power draw within the maximum power limit in all modes. However, costs for the drive electronics and the heating elements may be increased. In addition, the external dimensions of the heater may have to be increased in order to satisfy electrical creepage distance and other requirements.

In another preferred 2-element embodiment, each heater may include a first heating element of 1,250 watts and a second heating element of 250 watts. Such embodiment may require increased use of modulation to maintain appropriate power levels in some modes. In other embodiments, sizing of elements need not be identical for each heater, especially where heating requirements of the particular channels may be optimized for different uses, such as one for a main blood supply and one for cardioplegia.

Figure 6:
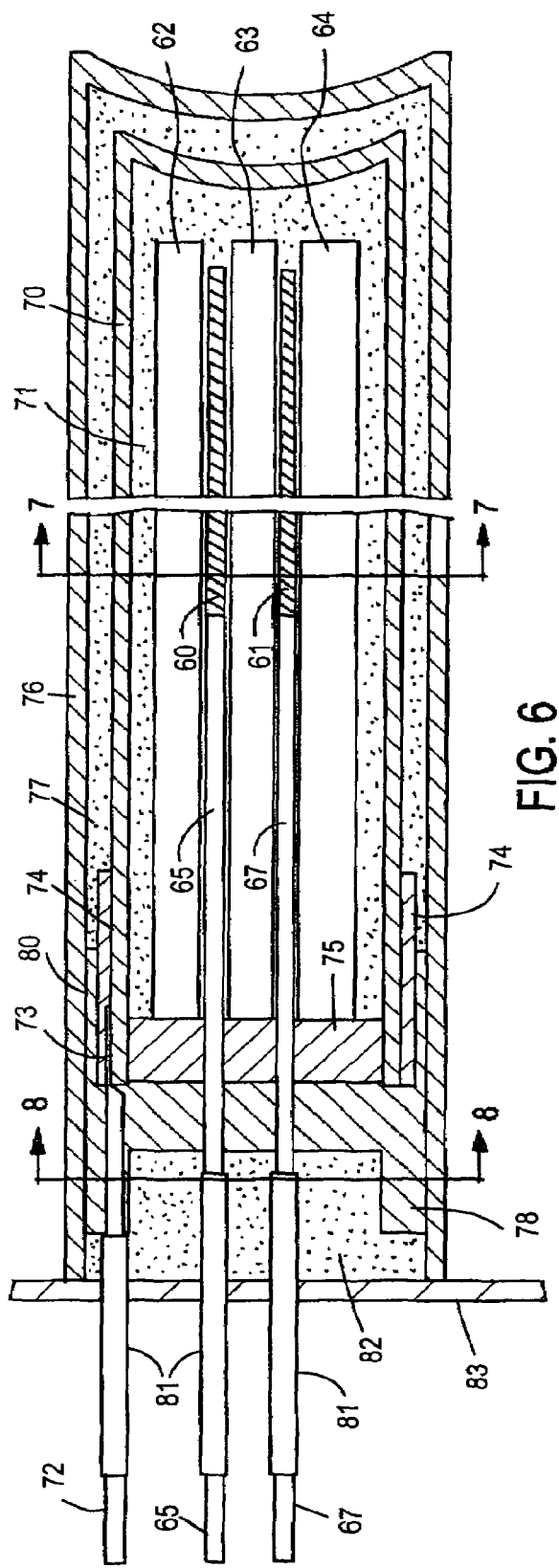
FIG. 6 is a partial cross section of a preferred embodiment of a heater having multiple heating elements.
Figure 8:
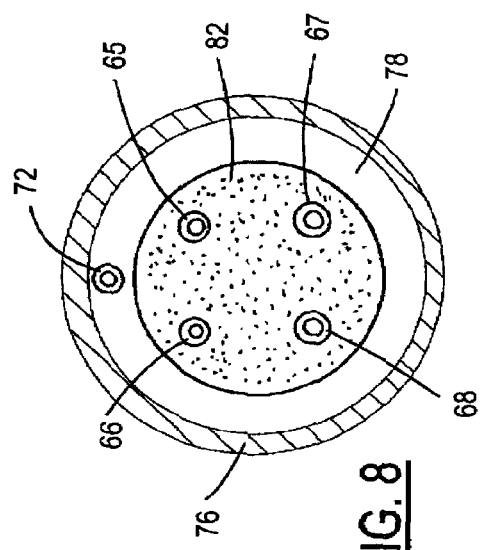
FIG. 8 is a lateral cross section of the heater as seen from line 8-8 of FIG. 6.
Figure 7:
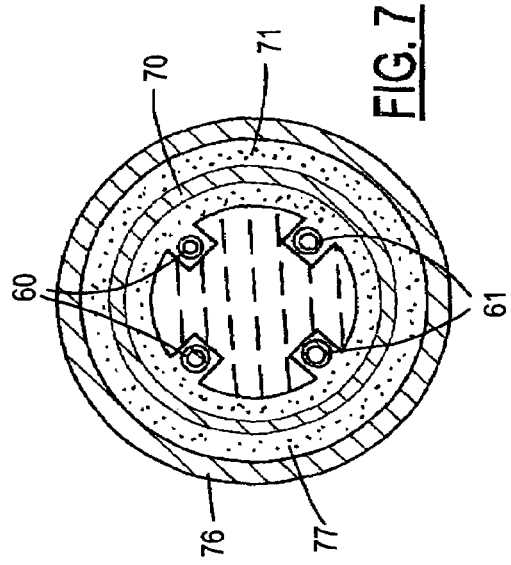
FIG. 7 is a lateral cross section of the heater as seen from line 7-7 of FIG. 6.

A preferred embodiment of a heater having two heating elements is shown in FIGS. 6-8. The heater is designed to meet electrical safety requirements for medical devices such as International Electrotechnical Commission (IEC) Publication 60601-1 (also UL 60601-1). The heater design satisfies the following requirements: 1) two independent heating elements are packaged in a single device with a diameter of approximately one inch and a length of six inches, 2) the heating elements affectively transfer thermal energy to the outer surface of the heater, 3) the heater meets dielectric strength, leakage current, and creepage/clearance distances as specified by UL 60601-1, and 4) the heater includes means for failing in a safe manner.

A first heating element 60 and a second heating element 61 are mounted on an elongated internal core 62 within longitudinal slots 63 and 64, respectively. Heating element 60 is connected to a pair of power pins 65 and 66, and heating element 61 is connected to a pair of power pins 67 and 68 partially extending through slots 63 and 64. Heating elements 60 and 61 are substantially U-shaped as are grooves 63 and 64, thereby preventing movement of heating elements 60 and 61 or power pins 65-68 in the vicinity of core 62. Internal core 62 is formed of a substantially rigid insulating material and preferably is comprised of ceramic having a high thermal transfer coefficient.

An inner isolation tube 70 receives core 62 and heating elements 60 and 61 in a non-contacting relationship. Tube 70 is closed at one end and is preferably formed of an electrically conducting metal such as stainless steel (e.g., 304 stainless steel). A granular insulation filler 71 is compacted between core 62 and inner isolation tube 70. In one preferred embodiment, a loose magnesium oxide (MgO) filler is placed in the space between core 62 and tube 70 and then compacted to improve its thermal transfer properties. Filler 71 is electrically insulating to prevent electrical coupling to tube 70.

A ground pin 72 has a terminal blade 73 for electrically connecting with inner isolation tube 70 by welding, for example. Grounding pin 72 is designed to handle at least 40 amps of current for at least 2 minutes. When installed in the heater/cooler system, the ground pin is connected to the chassis or earth ground to provide a means of shunting potentially hazardous currents in the event of a possible insulation breakdown. It may be desirable to add one or more additional grounding pins (e.g., a second grounding pin located diametrically opposite from pin 72) in order to provide redundancy and to enable testing of the ground connection (e.g., continuity testing).

An optional insulating sleeve 74 cylindrically wraps over the open end of inner isolation tube 70 to cover terminal blade 73. Sleeve 74 may be comprised of Teflon, for example.

After inserting core 62 into tube 70 and compacting filler 71, an inner end piece 75 is inserted into the open end of tube 70 to seal tube 70. Inner end piece 75 includes apertures for receiving pins 65-68 in a sealing relationship. Inner end piece 75 is electrically insulating and may be comprised of plastic.

The sealed inner isolation tube 70 is received by an outer isolation tube 76 in a non-contacting relationship. A granular insulation filler 77 (preferably MgO) is compacted between tubes 70 and 76. The granular insulation filler is thermally conductive and electrically insulating. Spacing between tubes 70 and 76 is maintained by filler 77 and by an outer end piece 78 having an inner flange 80 interposed between the tubes. Outer end piece 78 seals the open end of outer isolation tube 76 and receives power pins 65-68 and grounding pin 72 therethrough. Thus, outer isolation tube 76 is electrically floating from ground in order to protect both the system user and the patient from electrical shock. Tube 76 is preferably comprised of a conducting metal such as a nickel alloy (e.g., Incoloy 800).

Insulating sleeves 81 are provided on the power pins and grounding pin and then potting material 82 is inserted into the open end of outer isolation tube 76 for sealing the tube and supporting the power and grounding pins. A metal flange 83 is joined to outer tube 76 for mounting the heater unit to the heater/cooler system. Flange 83 is electrically insulated from the power pins and grounding pin by sleeves 81. Insulated wires (not shown) may be crimped over the power and grounding pins for connection to the system electronics. Insulating boots, (not shown) are preferably added over the insulated wires to provide a compact and manageable wire assembly.

In use, the reference wire connected to the grounding pin and inner isolation tube is connected to chassis ground. In addition, it may optionally be connected to an electrical circuit that monitors the amount of leakage current between the heating elements and the inner tube. If the insulating characteristics of the ceramic core between the heating elements or the insulation filler between the core and the tubes were to breakdown, the amount of leakage current could increase. The electrical circuit utilizes a threshold for indicating excessive leakage current. Once the threshold is crossed, the device detects a fault condition and shuts off power to the heating elements. This allows the heater to fail in a safe manner and prevents the patient and user from being exposed to excessive leakage current.

It is intended that the foregoing detailed description be regarded as illustrative rather than limiting, and that it be understood that it is the following claims, including all equivalents, that are intended to define the spirit and scope of this invention.

What is claimed is:

1. A dual-channel fluid temperature control apparatus for controlling temperature of cardiac fluids during surgery using power from an electrical convenience outlet having a power limit, said apparatus comprising:
    a first circulation channel for conveying a first heat exchange fluid;
    a second circulation channel for conveying a second heat exchange fluid;
    a first pump receiving said first heat exchange fluid to selectively pump said first heat exchange fluid within said first circulation channel;
    a second pump receiving said second heat exchange fluid to selectively pump said second heat exchange fluid within said second circulation channel;
    a first heater unit thermally coupled to said first heat exchange fluid and comprising a first plurality of independently actuatable heating elements each having a respective power consumption;
    a second heater unit thermally coupled to said second heat exchange fluid and comprising a second plurality of independently actuatable heating elements each having a respective power consumption;
    a cooling bath for selectably thermally coupling to said first and second heat exchange fluids; and
    a controller for selectably actuating said first and second pumps and said first and second pluralities of heating elements to selectably heat or cool said first and second heat exchange fluids such that power draw of all activated pumps and heating elements is maintained within said power limits
    wherein the combined power consumption of the first and second pluralities of heating elements together with the power consumption of the controller and the pumps is greater than the power limit, wherein the first plurality of heating elements includes a first individual heating element having a power consumption sufficiently small to enable the controller to maintain it fully on even when at least one of the second plurality of heating elements is fully on without exceeding the power limit, and wherein the second plurality of heating elements includes a second individual heating element having a power consumption sufficiently small to enable the controller to maintain it fully on even when at least one of the first plurality of heating elements is fully on without exceeding the power limit.

2. The apparatus of claim 1 wherein said controller activates selected ones of said heating elements having a combined maximum power consumption within said power limit.

3. The apparatus of claim 1 wherein said controller modulates selected ones of said heating elements of only one of said pluralities of heating elements to generate a combined actual power consumption that maintains said power draw within said power limit.

4. The apparatus of claim 1 further comprising:
    first and second temperature sensors thermally coupled to said first and second heat exchange fluids for generating first and second temperature measurements, respectively;
    wherein said controller modulates said selectably activated heating elements in response to said first and second temperature measurements to maintain a respective temperature of said first and second heat exchange fluids according to first and second predetermined setpoints, respectively.

5. The apparatus of claim 1 wherein said controller is responsive to actuation states of said pumps and to heating or cooling modes of said first and second circulation channels to determine actuation of said heating elements.

6. A dual channel heat exchange apparatus with first and second channels, said apparatus warming cardiac fluid using power from an electrical convenience outlet having a prescribed power limit, said apparatus comprising:
    a first heater in a first channel having independently energizable first and second electrical heating elements;
    a second heater in a second channel having independently energizable third and fourth electrical heating elements; and
    first and second fluid pumps for circulating a heat exchange fluid in said first and second channels, respectively, wherein each of said pumps consumes a predetermined power draw when its respective channel is active;
    said first and third heating elements selectably providing simultaneous, continuous activation to provide a combined power consumption together with both of said fluid pumps that is substantially equal to said power limit;

said second heating element selectably providing simultaneous continuous activation with said first heating element to provide a combined power consumption with said first heating element and said first fluid pump that is substantially equal to said power limit; and said fourth heating element selectably providing simultaneous continuous activation with said third heating element to provide a combined power consumption with said third heating element and said second fluid pump that is substantially equal to said power limit.

7. The apparatus of claim 6 wherein said second heating element is activated only when said third and fourth heating elements and said second fluid pump are continuously deactivated, and wherein said fourth heating element is activated only when said first and second heating elements and said first fluid pump are continuously deactivated.

8. The apparatus of claim 6 wherein said first and third heating elements have individual power consumptions that are substantially equal.

9. The apparatus of claim 6 wherein said second and fourth heating elements have individual power consumptions that are substantially equal.

10. The apparatus of claim 6 further comprising:
a controller for activating said heaters and said pumps according to a plurality of operating modes including a first mode wherein said first and second pumps are activated, said first and third heating elements are activated, and said second and fourth heating elements are continuously deactivated.

11. The apparatus of claim 10 wherein said first and third heating elements are continuously activated in order to obtain maximum heating.

12. The apparatus of claim 10 further including a second mode wherein said first pump is activated, said second pump is deactivated, said first and second heating elements are activated, and said third and fourth heating elements are continuously deactivated.

13. The apparatus of claim 10 further including a third mode wherein said first and second pumps are activated, said first and second heating elements are activated, and said third and fourth heating elements are continuously deactivated, and wherein activation of at least one of said first and second heating elements is modulated to maintain a total power consumption within said power limit.

14. The apparatus of claim 10 wherein at least one heating element activated in said operating modes is modulated to control heat transfer to said heat exchange fluid according to a temperature setpoint.

* * * * *